United States Patent [19]

Welch et al.

[11] 4,014,329
[45] Mar. 29, 1977

[54] METHOD AND APPARATUS FOR AUTOTRANSFUSION OF BLOOD

[75] Inventors: Joseph D. Welch, Galveston, Tex.; Barbara J. Doyle, Rochester, now by change of name Barbara J. Gutterman; Harvey A. Weintraub, Rochester, both of N.Y.; Ludovico Cerulli, Lucca, Italy

[73] Assignee: The Rochester General Hospital, Rochester, N.Y.

[22] Filed: July 3, 1975

[21] Appl. No.: 593,163

[52] U.S. Cl. .......................... 128/214 R; 128/276; 137/205

[51] Int. Cl.² ..................... A61M 5/14; A61M 1/02

[58] Field of Search ....... 128/214 R, 214 C, 214 F, 128/214.2, 230, 276–278; 137/205

[56] References Cited

UNITED STATES PATENTS

| 2,766,907 | 10/1956 | Wallace | 222/94 |
|---|---|---|---|
| 3,153,414 | 10/1964 | Beall et al. | 128/327 X |
| 3,492,991 | 2/1970 | Dyer | 128/214 R |
| 3,680,560 | 8/1972 | Pannier et al. | 128/276 |
| 3,719,197 | 3/1973 | Pannier et al. | 137/205 |
| 3,866,608 | 2/1975 | Reynolds et al. | 128/276 |

*Primary Examiner*—Dalton L. Truluck
*Attorney, Agent, or Firm*—George W. Shaw

[57] ABSTRACT

A method and device is provided for autotransfusion of blood during surgery. The shed blood is retrieved from the surgical field via a receiving vessel located within a vacuum chamber and under less vacuum than the vacuum applied to the chamber. The vacuum in the receiving vessel draws blood from the surgical field into the receiving vessel where it is first collected and then passed to a second vessel. The blood is transferred from the second vessel to the patient during reinfusion. Suitable filters are provided for removing any blood clots or bits of tissue before the blood is reinfused.

10 Claims, 3 Drawing Figures

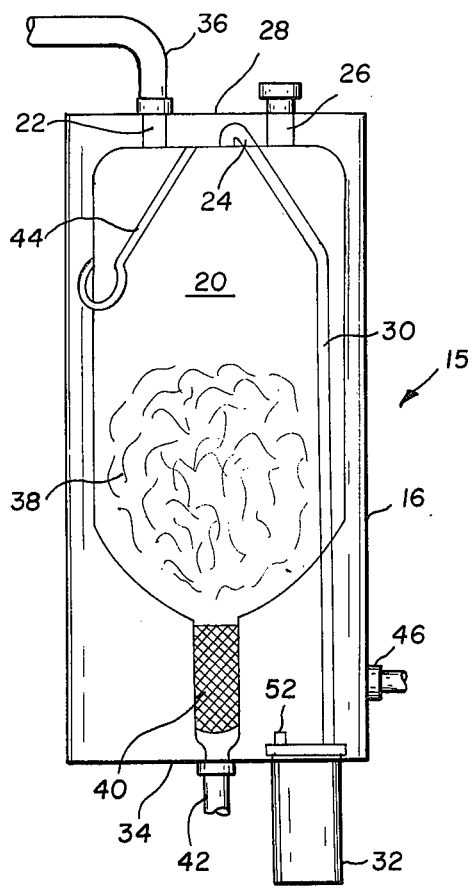
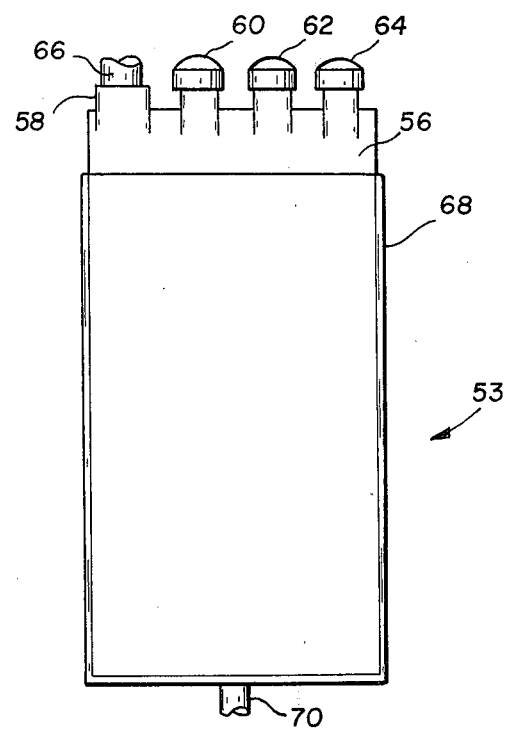
FIG. 2
FIG. 3

METHOD AND APPARATUS FOR AUTOTRANSFUSION OF BLOOD

BACKGROUND OF THE INVENTION

1. Field of the Invention

This invention relates to devices for harvesting a patient's own blood lost during surgery, defoaming and filtering the blood, and readministering it to the patient intravenously.

2. Description of Prior Art

Because of the danger to a patient's health resulting from the loss of any quantity of blood, either the result of injuries or during surgery, it has become common practice to maintain the patient's blood volume by the transfusion of homologous banked blood. However, there are several well known complications resulting from the administration of homologous blood. In some instances, the homologous banked blood has carried serum hepatitis. In other instances, patients have had acute reactions to transfusion or have had blood types that were difficult to cross match because of complexities in the blood chemistry. In order to reduce or eliminate the demand for homologous banked blood, attempts have been made over the years to collect the patient's own blood lost during surgery and return it to him. In early attempts, surgeons collected the blood from the abdomen by a ladle or cupped hands and placed it in basins or flasks containing sodium citrate. This blood was then returned to the patient intravenously. Later developments included the collection of blood by a suction line and filtering the blood through gauze and then readministering it to the patient. These attempts were cumbersome and subject to contamination.

Early attempts to provide a closed means for withdrawing the blood utilized glass or pyrex vessels for receiving the blood. It was a simple matter to apply vacuum to such vessels which were provided with suitable inlet hoses and probes for extracting the blood for the surgical field. However, it was found that the hard surfaces of the receiving vessels caused considerable damage to the blood components, and it was evident that less damage would occur to the blood if a soft plastic bag, such as that used in blood transfusion work, could be used. However, early attempts to apply vacuum to a blood collection bag failed, because atmospheric pressure caused the bag to collapse under the action of the vacuum. One of the objects of the present invention is to eliminate the need for the hard glass receiving vessels and allow the use of the softer plastic receiving vessels.

In recent years, a closed circuit autotransfusion device has been developed consisting of a roller pump for withdrawing the blood from a surgical field and transferring it to a rigid sterile reservoir at an elevated location. The blood collected in the reservoir is then returned to the patient via direct pressure produced by the roller pump. Filtering is accomplished in the reservoir and in the return lines.

However, this device has a distinct disadvantage in that once the reservoir has been filled or partially filled with blood, a layer of blood remains on the inside of the reservoir thereby falsely giving the appearance that a considerable quantity of blood is in the reservoir when actually the reservoir may be nearly empty. This creates a dangerous situation since the operator may continue to reinfuse blood from the reservoir to the patient. As the blood is being reinfused under direct pressure from the action of the roller pump, if the blood supply in the reservoir is exhausted, air from the reservoir will be forced into the patient causing an air embolism with fatal results. There have been several cases where this has happened. Despite this danger and the cost of such equipment, it is currently available commercially and is in use in many hospitals.

A second device that has had limited use utilizes a standard plastic blood collection bag located inside a vacuum chamber. When a vacuum is applied to the chamber in the area between the chamber and the blood bag, the bag is caused to expand, thereby exerting a vacuum or suction on the inlet line leading from the bag to the patient. Although this device eliminates the use of a roller pump, it is necessary to stop the device when the bag is full, open the vacuum chamber, remove the full bag of blood, connect a new collapsed, plastic blood bag to the suction line, and transfer the full bag to an elevated stand whereby the blood was reinfused through the action of gravity into the patient.

Although this second apparatus has the advantage of eliminating the roller pump, it cannot be operated continuously, as it requires certain down time for removing the full bag of blood and placing an empty bag in its place, reclosing the vacuum chamber, and again applying vacuum to the area between the bag and the chamber to cause the bag to expand and create a vacuum on the inlet line to the bag. In addition, this device is not capable of use in those situations where any appreciable volume of air will be drawn into the bag. This device would not be usable in the normal surgical situation where the volume of air to blood drawn into the bag would be 10 to 1 or more, because unless the bag is substantially full of blood, the anticoagulant material that is in the bag prior to its use will be in excess of the normally desired amount. Moreover, if unwanted air is drawn into the bag, it will require frequent changing of the bags to accommodate any volume of blood. Consequently, because of its inability to accommodate any appreciable volume of air, this device is limited to use in cases of hemothorax.

SUMMARY OF THE INVENTION

The present invention has as its object to provide an improved autotransfuion device that uses only soft plastic bags for receiving the blood, can be operated continuously, eliminates the need for a roller pump, and at the same time avoids the possibility of air embolism. In addition, in the present device the blood may be collected and held in a reservoir pending a decision by the operating staff whether to reinfuse the blood. While this determination is being made, additional blood may be withdrawn from the surgical field for possible subsequent use.

The present device comprises a receiving vessel, preferably a standard plastic blood collection bag, that is located within a vacuum chamber. Vacuum is applied to the bag and to the area between the bag and the chamber but at different levels. The vacuum between the bag and the chamber is greater than the vacuum applied to the bag so that the bag is caused to expand, while at the same time vacuum applied to the bag passes through the bag and the inlet line extending from the bag to the patient. When the receiving vessel is substantially full or whenever it is desired to reinfuse the blood to the patient, a valve located in a discharge line from the receiving vessel is opened allowing the blood to flow, by gravity and without the addition of air to the blood, to a second or holding vessel. From the holding vessel, the blood is caused to flow through suitable filters to remove impurities and to the patient for reinfusion. Although the bood may be caused to move from the holding vessel to the patient solely by gravity, it is preferred to provide positive means for accomplishing this as by use of an expandible sleeve or envelope surrounding the holding vessel, which expands when supplied with positive pressure and thereby squeezes the holding vessel and expells the blood therefrom to the patient.

Since the positive pressure is applied to the blood indirectly, as through the expansion of the sleeve surrounding the holding vessel, there is no air to blood interface, as in the case of the device described earlier using a roller pump, and thus there is no chance for an air embolism to occur. In addition, the present device is capable of use in those situations where great quantities of air may be drawn in with the retrieved blood or between periods of retrieval. This undesired air presents no problem, because it merely passes into the receiving vessel and is drawn from the vessel by the vacuum circuitry so that it does not mix with the blood in the receiving vessel and the device can accommodate a wide range of air-to-blood ratios without loading up the device with unwanted air, as in the case of the second prior art device described earlier, or setting up the situation where an air embolism might occur as with the first type of prior art device described.

BRIEF DESCRIPTION OF THE DRAWINGS

FIG. 2 is an enlarged elevational view of the upper or retrieval portion of the device; and FIG. 3 is an enlarged elevational view of the lower portion of the device constituting the administration system.

DETAILED DESCRIPTION

Figure 1:
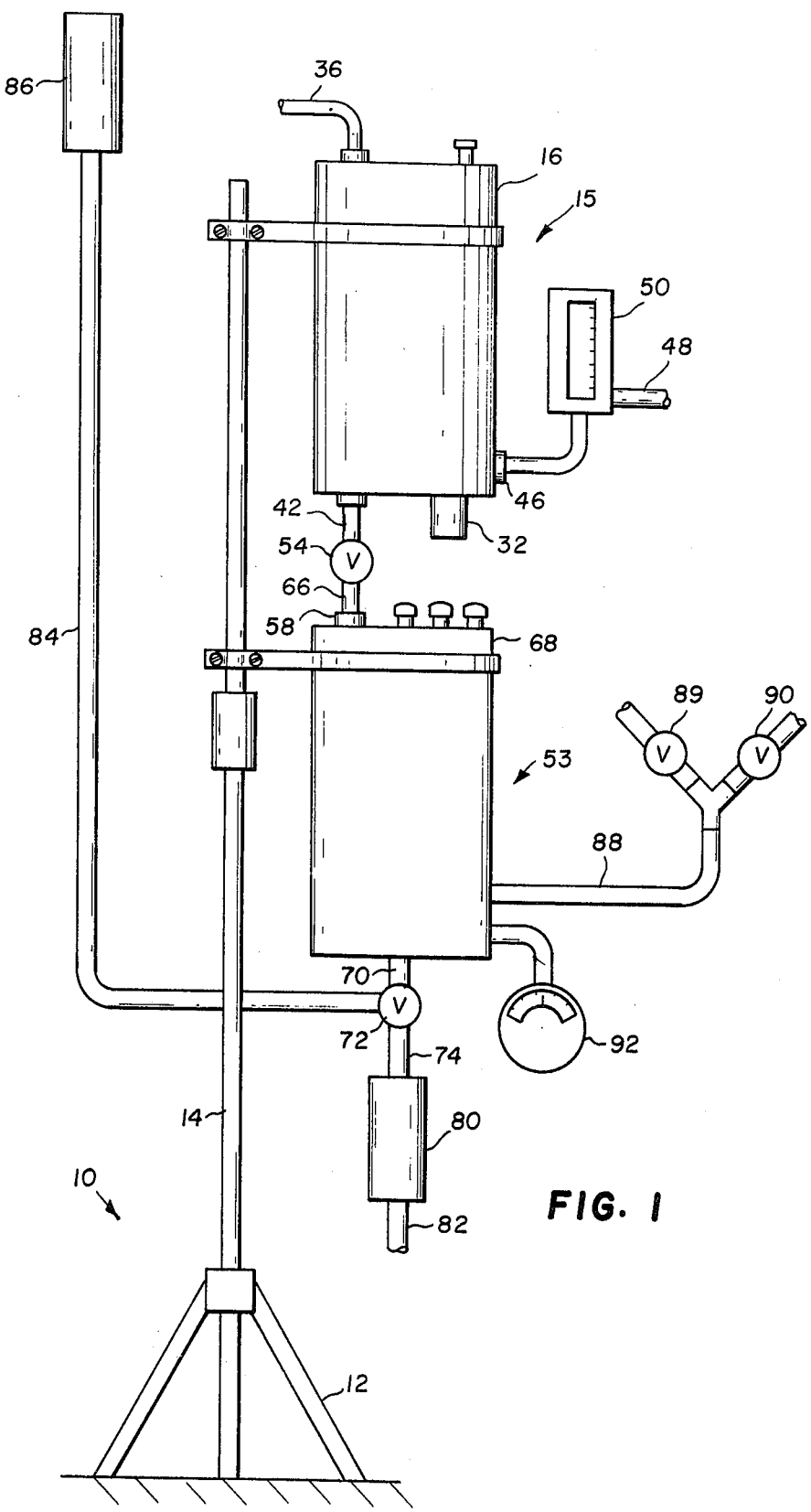
FIG. 1 is a front elevational view showing a device embodying the present invention

The present invention preferably comprises a supporting frame 10 comprising a base 12 and vertically extending telescopic column 14. Supporting frame 10 is well known and forms no part of the present invention.

The upper portion of the device constitutes a retrieval system and comprises a transparent plastic cylinder 16 which is secured to the upper portion of column 14 by suitable clamping means 18. Mounted within cylinder 16 is a soft, plastic blood collection bag or vessel 20 such as that now used in certain cardio-pulmonary operations for collecting blood. Bag 20 has three inlet ports 22, 24 and 26, as shown in FIG. 2. Ports 22 and 26 extend through the upper end 28 of cylinder 16 for purposes to be hereafter described. The remaining port 24 is connected by a small plastic tube 30 to a cylindrical overflow trap 32 preferably located in the bottom wall 34 of cylinder 16.

The openings in top wall 28 through which ports 22 and 26 extend are preferably sealed around the ports by suitable caulking or gasket means not shown. Port 22 is connected to a length of plastic tubing 36 which leads to the patient and serves as the suction line for retrieving the blood from the surgical field. Port 26 is sealed with an imperforate plug that may be pierced by a syringe or needle and may be used for adding drugs, antibiotics, or other solutions to the blood collected within bag 20.

Bag 20 is partially filled with a mass of silicone coated steel wool or steel sponge 38 which is a well known material for defoaming blood. At the lower end of bag 20, there is a built-in filter 40 which is between the major portion of the bag and an outlet line 42 which extends through lower wall 34 by means of a substantially air-tight connection in the same manner as ports 22 and 26 extend through the upper wall of the cylinder. Bag 20 is preferably provided with an interrupted crease or clamp 44 as shown in FIG. 2. The purpose of the interrupted crease or clamp is to prevent the blood from falling directly from inlet port 22 onto steel wool 38 and to cause the blood to flow along the inside walls of the bag thereby reducing the damage to the blood components.

Chamber 20 is provided with an outlet 46 to which a source of vacuum (not shown) is connected by means of plastic tubing 48. A vacuum flow gage 50 is inserted in the line to allow the operator to control the amount of vacuum applied to chamber 16 and bag 20 and thus control the amount of vacuum applied to blood inlet line 36. Although port 46 is shown adjacent the bottom of cylinder 16, it could be located at any convenient position in the chamber. Overflow trap 32 which is connected at one side to bag 20 by means of tubing 30 has a second passageway 52 connecting the trap to chamber 16 so that negative vacuum or negative pressure applied to the inside of chamber 16 also acts through overlfow trap 32, line 30 and through port 24 to the inside of bag 20.

Thus, it will be seen that when a vacuum or negative pressure is applied to line 48, the interior of vacuum chamber 16 is placed under a vacuum, and so also is the interior of bag 20. However, due to the throttling effect of line 30, the vacuum applied to the interior of bag 20 is less than the vacuum applied to chamber 16. As a result, bag 20 expands, while at the same time a vacuum is provided in inlet line 36 for drawing the blood from the patient into bag 20.

Blood from the receiving vessel or bag 20 could be run through suitable filters and directly back to the patient by locating the retrieval system at an elevated position relative to the patient so that the blood would flow by gravity to the patient. However, it is preferred to provide a second vessel or reservoir as part of an administration system shown generally at 53 for holding the blood after it has been collected to provide the doctors operating on the patient the option of determining whether and when they wish to reinfuse the patient's own blood. This second system allows for the continuous retrieval and reinfusion of blood and for infusion of blood under pressure, but without there being any possibility of air being forced into the patient. To this end, a valve 54 is mounted on outlet line 42 for controlling the flow of blood from receiving vessel 20 to the administration system. Valve 54 may be a sophisticated air controlled valve or may simply be a clamp that can be quickly and easily opened and closed by the operator. In any event, after passing through valve 54, the blood flows by gravity to a second vessel 56 which peferably is a soft plastic blood holding bag of known construction. Bag 56 is initially completely evacuated and is provided with a series of inlet ports 58, 60, 62 and 64. Inlet port 58 is connected to line 42 below valve 54. Remaining ports 60, 62 and 64 are closed by imperforate plugs in much the same manner as inlet port 26 in the upper bag, but may be readily pierced by a needle for insertion of drugs, antibiotics, or for drawing off a sample of the patient's blood for analysis. In this manner, bag 56 may be partially or completely filled with blood without the addition of air or the use of a damaging roller pump.

Bag 56 is preferably supported within a pneumatic sleeve or cuff 68 which in turn is attached to column 14 by suitable means not shown. Bag 56 has an integrally formed outlet line 70 that extends through a suitable opening in pneumatic sleeve 68 as shown. Outlet line 70 is connected to a three-way valve 72 for purposes to be hereafter described. From valve 72, a length of tubing 74 leads to a micro filter 80. From filter 80, a further line 82 leads to the standard intravenous needle for reinfusing the blood to the patient. Valve 72 and filter 80 are of known construction and form part of a standard blood administration system and have been chosen for use because of their known reliability and easy availability. Although the construction of the valve and filters do not form part of the invention, it is part of the present invention to include some suitable filtering and valve means as part of the preferred autotransfusion system.

Valve 72 is connected by means of a suitable tube 84 to a standard intravenous bag 86 which may contain a saline solution or the like. It is evident that by proper positioning of three-way valve 72 the patient's blood or the intravenous solution may be caused to pass through line 74 and filter 80 and hence into the patient. The purpose of providing valve 72 and the intervenous solution bag 86 is to allow the doctors to easily administer fluid to the patient and to provide a solution for flushing line 74 and associated valve and filter during interruptions in the return of the blood to the patient. Obviously, this is not a necessary part of the invention, but is included as a further refinement.

Pneumatic sleeve 68 is connected by means of tubing 88 to a source of positive pressure by means of a valve 89 and to a source of suction or negative pressure by means of a valve 90. A pressure gauge 92 is connected to pneumatic sleeve 68 for monitoring the pressure applied to bag 56 through pneumatic cuff 68.

At the start of the operation, pneumatic cuff 68 is in deflated condition because it is connected to a source of negative pressure through valve 90. In this condition, the cuff readily allows bag 68 to expand to accommodate the volume of blood released from upper bag 20. When the operator desires to expel the blood from bag 56, valve 90 is closed, and valve 89 opened to supply positive pressure to tube 88 which in turn inflates pneumatic sleeve 68 thereby squeezing bag 56 and forcing the blood therein through outlet 70 and through the associated valve and filter means to line 82 and thence to the patient for reinfusion. The pressure applied to cuff 68 may be observed on gauge 92.

Thus, it will be seen that the invention provides an improved, economical and practical device for collecting blood from a patient and subsequently filtering the blood and reinfusing the same into the patient. The device does not use hard pyrex containers or damaging roller pumps, but rather utilizes the soft plastic blood bags that have proven highly desirable for use in handling blood. In addition, the various components through which the blood flows may be readily provided in sterile, sealed condition for easy assembly and use. The present device does not require any special facilities not normally found in an operating room but rather require only a source of vacuum or negative pressure and a source of positive pressure. There are no parts that are apt to cause electrical sparks or discharge which would be hazardous in an operating room where explosive anesthetics might be used, and because of the transparent nature of the vacuum chamber and the plastic bags, the operator at all times may visually check the operation of the device and make any adjustments deemed desirable. The blood, when collected, may be immediately re-infused into the patient or it may be stored a period of time while the doctors operating on the patient determine whether the blood should be re-infused and if so, at what point during the operating procedure. There is no danger of air embolism because the pneumatic force is not directly applied to the blood. The whole sequence is continuous, free of maintenance problems and has proven itself to be highly reliable.

The terms "infuse" and "reinfused" are used interchangeably herein. Although the blood picked up by the inventive device is that of the patient and is being returned to the patient and thus may be thought of as being reinfused into the patient, since this is the first infusion, it may also be properly throught of as being infused into the patient.

Persons wishing to practice the invention should remember that other embodiments and variations can be adapted to particular circumstances. Even though one point of view is necessarily chosen in describing and defining the invention, this should not inhibit broader or related embodiments going beyond the semantic orientation of this application but falling within the spirit of the invention. For example, vacuum chamber 16 may be of varied shape and may be made of different materials; and whereas upper bag 20 and lower bag 56 are shown with auxiliary ports for administration of drugs or other solutions, such are optional and not part of the present invention.

We claim:

1. A device for infusing blood from a patient wherein the blood may be continuously retrieved from and infused into the patient, comprising:
    a. a vacuum chamber including means for applying a vacuum thereto;
    b. a separate receiving vessel located within said chamber;
    c. throttling means associated with said vacuum means for applying a differential vacuum to said chamber and said receiving vessel whereby the vacuum applied to said chamber is greater than the vacuum applied to said receiving vessel;
    d. a pick-up line connected to said receiving vessel and of sufficient length to extend to the source of blood to be drawn into said receiving vessel;
    e. a second vessel located outside said chamber and at a lower elevation than said chamber;
    f. a fluid connection from said receiving vessel to said second vessel including valve means independent of the action of said pick-up line whereby said blood may flow by gravity from said receiving vessel to said second vessel while maintaining said vacuum applied to said receiving vessel so that additional quantities of said blood may be drawn into said receiving vessel as said blood flows into said second vessel;
    g. means engaging said second vessel for expelling said blood from said second vessel for delivery to said patient; and h. filter means in said device for cleaning the blood and removing impurities.

2. The device of claim 1 wherein said receiving vessel is a collapsible, plastic bag.

3. The device of claim 1 wherein said receiving vessel has a sterile port for administration of drugs, antibiotics, or the like, in fluid form.

4. The device of claim 1 wherein said second vessel has a sterile port for administration of drugs, antibiotics, or the like, in fluid form.

5. The device of claim 1 wherein said second vessel is a collapsible, plastic bag, and wherein said receiving vessel has a sterile port for administration of drugs, antibiotics, or the like, in fluid form.

6. The device of claim 1 wherein said second vessel is a collapsible, plastic bag and has a sterile port for administration of drugs, antibiotics, or the like, in fluid form.

7. The device of claim 1 wherein said second vessel is a collapsible, plastic bag.

8. The device of claim 7 wherein the means for expelling said blood from said second vessel comprises a double wall flexible container which, when inflated, squeezes said second vessel for expelling said blood from said second vessel.

9. The device of claim 7 wherein said first vessel is a collapsible, plastic bag, wherein said second vessel has a sterile port for administration of drugs, antibiotics, or the like, in fluid form, and wherein said filter means are located downstream of said receiving vessel.

10. The method of infusing blood from a patient comprising the steps of:
 a. retrieving the blood continuously from the patient by suction into a receiving vessel located within a vacuum chamber
 b. providing a differential vacuum between said receiving vessel and said vacuum chamber such that said vacuum chamber is under a greater vacuum than said receiving vessel;
 c. transferring said blood from said receiving vessel to a second vessel outside of said vacuum chamber without interrupting the flow of said blood to said vacuum chamber.
 d. transferring said blood from said second vessel to said patient; and
 e. filtering said blood before returning said blood to said patient for cleaning said blood and removing impurities.

* * * * *